United States Patent
Allman

(10) Patent No.: US 11,800,852 B2
(45) Date of Patent: Oct. 31, 2023

(54) ANIMAL SURGERY PROTECTIVE SLEEVE

(71) Applicant: LICK SLEEVE LLC, Austin, TX (US)

(72) Inventor: David Allman, Austin, TX (US)

(73) Assignee: LICK SLEEVE LLC, Austin, TX (US)

( * ) Notice: Subject to any disclaimer, the term of this patent is extended or adjusted under 35 U.S.C. 154(b) by 265 days.

(21) Appl. No.: 17/302,564

(22) Filed: May 6, 2021

(65) Prior Publication Data

US 2021/0251187 A1    Aug. 19, 2021

Related U.S. Application Data

(60) Division of application No. 16/883,059, filed on May 26, 2020, now Pat. No. 11,039,600, which is a continuation of application No. 15/426,006, filed on Feb. 6, 2017, now abandoned.

(60) Provisional application No. 62/293,323, filed on Feb. 9, 2016.

(51) Int. Cl.
| | |
|---|---|
| *A01K 13/00* | (2006.01) |
| *A01M 29/00* | (2011.01) |
| *A61D 9/00* | (2006.01) |
| *A61B 5/0205* | (2006.01) |
| *A61B 5/00* | (2006.01) |
| *A01K 29/00* | (2006.01) |
| *A61B 5/11* | (2006.01) |

(52) U.S. Cl.
CPC ............ *A01K 13/007* (2013.01); *A01M 29/00* (2013.01); *A61B 5/02055* (2013.01); *A61B 5/6828* (2013.01); *A61D 9/00* (2013.01); *A01K 29/005* (2013.01); *A61B 5/1118* (2013.01)

(58) Field of Classification Search
CPC ....... A01K 13/007; A01K 13/006; A61D 9/00
USPC ........................................................ 119/850
See application file for complete search history.

(56) References Cited

U.S. PATENT DOCUMENTS

| | | |
|---|---|---|
| 2,443,831 A | 6/1948 | Miller |
| 4,744,333 A | 5/1988 | Taylor |
| 5,341,765 A | 8/1994 | McComb |
| 6,151,873 A | 11/2000 | Rogers |

(Continued)

FOREIGN PATENT DOCUMENTS

| | | |
|---|---|---|
| FR | 2843539 B1 | 6/2005 |
| FR | 2924329 A1 | 6/2009 |
| GB | 2029231 A | 3/1980 |

OTHER PUBLICATIONS

"How to Split a Dog's Leg", published by www.wikihow.com (Year:2015), NPL in U.S. Appl. No. 15/426,006, Document Not Available for Download in Patentcenter.

*Primary Examiner* — Magdalena Topolski
*Assistant Examiner* — Marisa V Conlon
(74) *Attorney, Agent, or Firm* — Craige Thompson; Thompson Patent Law; Timothy D. Snowden

(57) ABSTRACT

A pet protection system includes a leg portion having a first end having a first cross-section having a flexible opening to insert a pet foot therethrough; an angled portion coupled to the first end and having a second cross-section greater than the first cross-section; and a second end coupled to the angled portion, wherein the second end has a third cross-section greater than the second cross-section; and a body portion coupled to the leg portion, the body portion forming a loop that fits securely on a body of the pet.

20 Claims, 7 Drawing Sheets

(56) References Cited

U.S. PATENT DOCUMENTS

| | | |
|---|---|---|
| 6,240,882 B1 | 6/2001 | Gross |
| 6,595,162 B1 | 7/2003 | Hibbert |
| 8,161,668 B2 | 4/2012 | Ketzenberg et al. |
| 8,316,626 B2 | 11/2012 | Sherer |
| 8,424,495 B2 | 4/2013 | Rivera-Brutto |
| D692,625 S | 10/2013 | Kok-Duson |
| 8,707,910 B1 * | 4/2014 | Koll .................... A01K 13/006 119/850 |
| 8,733,296 B1 * | 5/2014 | Douglas ............... A01K 13/006 119/856 |
| D796,123 S | 8/2017 | Leskosek |
| D799,757 S | 10/2017 | Erwin |
| 9,936,677 B1 | 4/2018 | Slater |
| 9,956,065 B2 | 5/2018 | Flickinger et al. |
| D858,902 S * | 9/2019 | Klemsz ........................ D30/144 |
| D863,697 S * | 10/2019 | Carlson ........................ D30/145 |
| 2005/0034686 A1 | 2/2005 | Spatt |
| 2007/0074677 A1 | 4/2007 | Behme |
| 2008/0177210 A1 | 7/2008 | Larson |
| 2009/0173290 A1 | 7/2009 | Freitag |
| 2009/0266310 A1 | 10/2009 | Behme |
| 2010/0031898 A1 | 2/2010 | Page |
| 2011/0017151 A1 | 1/2011 | Simoni |
| 2013/0008393 A1 | 1/2013 | Backman et al. |
| 2015/0245897 A1 | 9/2015 | Hasebi et al. |

* cited by examiner

ANIMAL SURGERY PROTECTIVE SLEEVE

This application is a Divisional of and claims the benefit of U.S. application Ser. No. 16/883,059 titled "ANIMAL SURGERY PROTECTIVE SLEEVE," filed by David Allman on May 26, 2020; which application is a Continuation of and claims the benefit of U.S. application Ser. No. 15/426,006 titled "ANIMAL SURGERY PROTECTIVE SLEEVE," filed by David Allman on Feb. 6, 2017; which application claims the benefit of U.S. Provisional Application Ser. No. 62/293,323, titled "Protective leg sleeve for animals," filed by David Allman on Feb. 9, 2016. This application incorporates the entire contents of the foregoing application(s) herein by reference.

BACKGROUND

Anterior cruciate ligament (ACL) surgery [also called Cranial Cruciate Ligament (CCL) surgery] is the most common orthopedic surgery performed in dogs. When the ACL ruptures or is torn, the joint becomes unstable causing the femur and tibia to move back and forth across each other leading to severe pain and arthritis. ACL injury can occur from trauma or more commonly from a genetics based degeneration.

Typical surgical techniques used to treat ACL injuries in dogs require an incision on the leg. The most common surgical techniques used to treat this injury in dogs are the lateral fabellar suture and the tibial plateau leveling osteotomy (TPLO). During these procedures non absorbable surgical implants are used to restore stability to the joint.

Anytime surgical stainless steel or other implant materials are placed underneath the skin of dogs or people the surgical sight is significantly more prone to serious infection. The most common cause of infection in dogs is their own licking of the incision. In addition to licking the incision dogs can cause damage to their incisions by pawing/scratching, rubbing on objects, rolling in dirt, or from other pets in the household licking them.

Surgical site infections in animals are a serious post operative complication. Infections lead to severe pain, delayed healing, additional hospitalization, increased cost, exacerbation of other health issues (diabetes, kidney failure, heart disease, etc.), amputation of the limb, and death.

Extreme challenges still exist in veterinary medicine to prevent pets from damaging their incisions. The traditional plastic cone over the head of the animal variously known as the "E-collar" (short for "Elizabethan collar"), the "lampshade," the "satellite dish," or "the cone of shame" is the most common solution to the problem of postoperative incision complications and other areas in need of self-trauma avoidance. Other objects have been created that can be affixed around the pet's neck (bite not collars, doughnuts, soft e-collars etc.) and these in combination with the cone have been proposed. However, the same problems remain; discomfort to the pet and person, damage to household items, improper fitting, inability to eat or drink when wearing device, difficulty walking, unable to fit in kennel or through dog door, and more. As a result, it is well known most dog owners are unable or unwilling to keep the cone on the dog for the required amount of time.

Fabric covers have been developed for the limbs of animals in various shapes and sizes. These covers are either front limb specific, only cover a portion of the leg, or require fixation to a harness or torso cover to stay in place. The problem with these other fabric coverings is their inability to stay snugly in place without sliding, bunching or falling off. Some models do not cover enough surface area, or have to go over both legs to stay in place. Often times the materials are of insufficient quality, the pets do not tolerate the design, or the cost of the product is too high.

Given these problems and more, veterinarians, pets and pet owners are still in need of additional solutions to prevent their pet's self destruction.

SUMMARY

In one aspect, a pet protection system includes a leg portion having a first end having a first cross-section having a flexible opening to insert a pet foot therethrough; an angled portion coupled to the first end and having a second cross-section greater than the first cross-section; and a second end coupled to the angled portion, wherein the second end has a third cross-section greater than the second cross-section; and a body portion coupled to the leg portion, the body portion forming a loop that fits securely on a body of the pet.

In another aspect, a method to protect a pet using a sleeve includes with the pet lying down to prevent injury or falling, placing the first end portion on a leg; stretching the ankle cuff portion of the sleeve over the pet's paw; moving the pet into a standing position; placing the body portion on an inside of the leg and wrapping the body portion around a belly of the pet towards an opposite leg; and strapping the body portion with the second portion to produce a tight fit.

Advantages of the system may include one or more of the following. The sleeve is washable, reusable, and reversible. The sleeve is easy to store and easy to put on and remove and stays in place on the dog with no need to clip to the dog's collar or harness. The sleeve covers the whole leg instead of just the incisional area. It reduces anxiety for both the dog and the owner. The sleeve minimizes problems from self-trauma situations in pets. The sleeve reduces the need for re-stitching incision sites and reduces the cost associated with antibiotics from the pet's scratches. The system enhances the healing of pets by reducing the pet's ability to access, scratch, lick or chew on their healing wound or surgical incision. This is done without aggravation to the pet, improving compliance with veterinary recommendations to keep the sleeve in place for the specified duration required for healing. Additionally, the sleeve protects the pet and fragile items in the house, unlike the cone where the dog can barrel headlong into household items or people. The sleeve is comfortable for the dog, unlike the cone that can cause dogs to howl, paw, turn in an endless circle, or perform alligator death rolls on the ground, etc. whenever the pet is wearing a cone. The sleeve is also durable, unlike cones whose edges can be destroyed, rendering the cones useless. The sleeve could also be used as a supplement to the existing plastic cone. For a majority of pets these sleeves will allow for a cone free recovery.

DESCRIPTION

Figure 1:
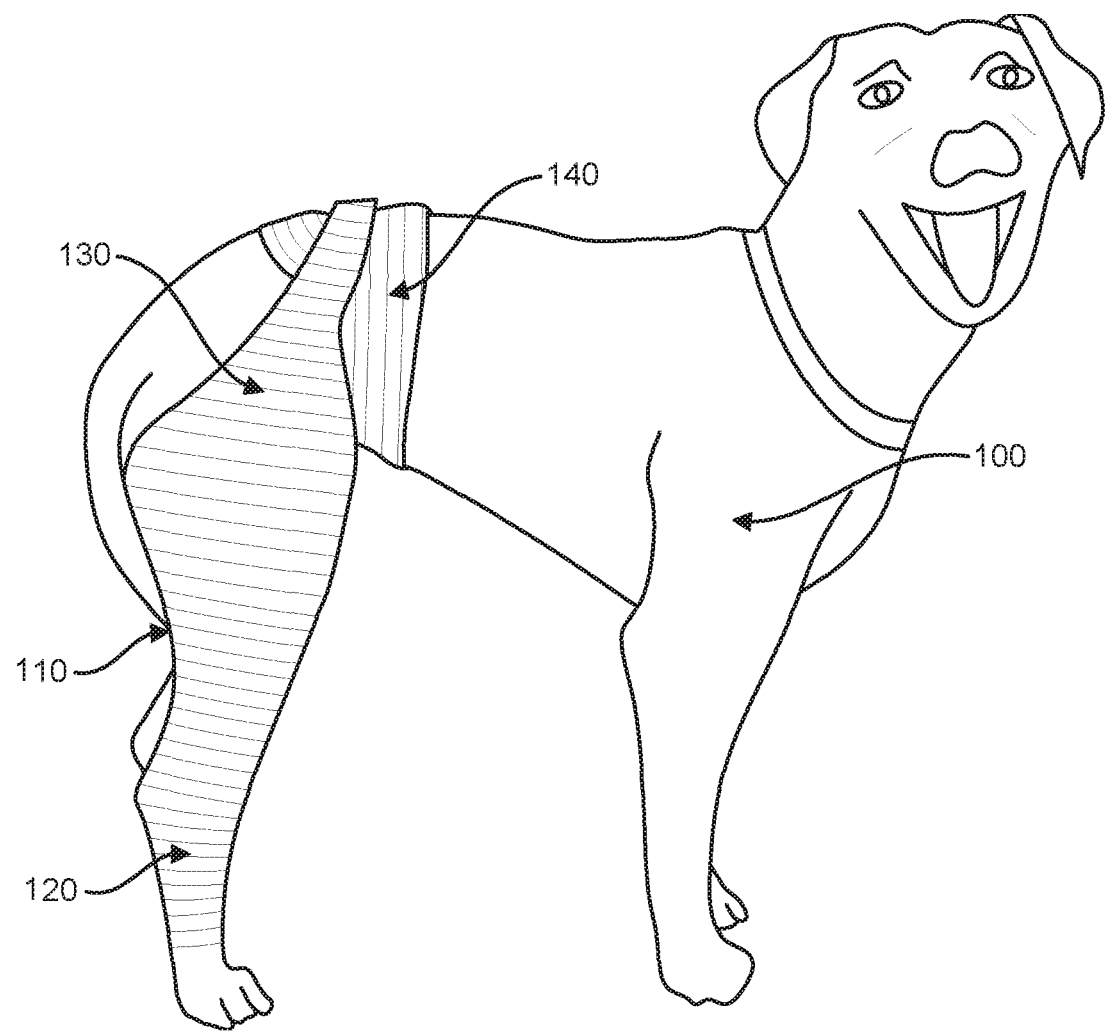
FIG. 1 shows a perspective view of an outer face of a sleeve system on a pet.
Figure 2:
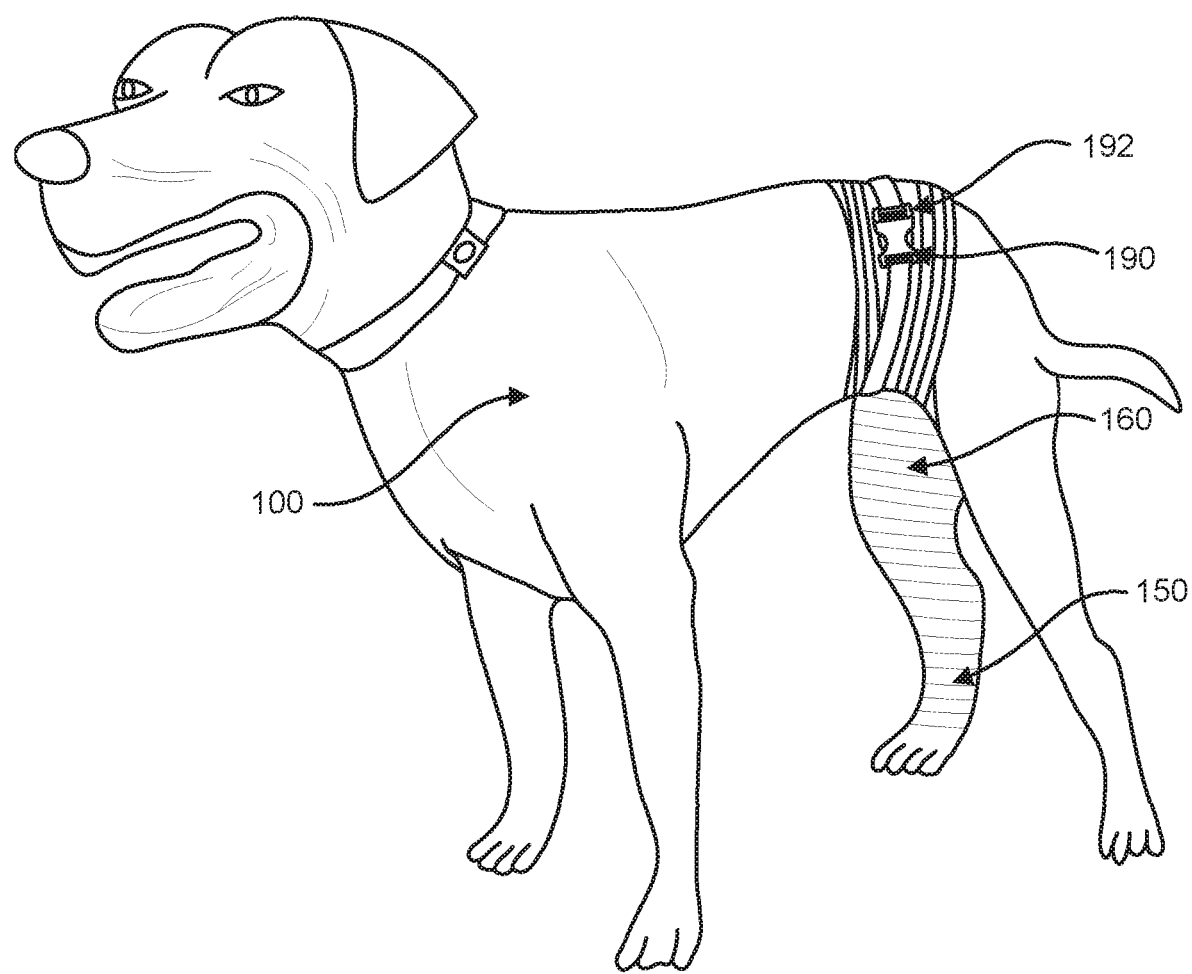
FIG. 2 shows a perspective view of an inside face of the sleeve system on a pet.

FIGS. 1-7 show an exemplary protection system for a pet 100. FIG. 1 shows a perspective view of an outer surface of a sleeve system on a pet while FIG. 2 shows a perspective view of an inside surface of the sleeve system on the pet. The system has a leg portion 110 (FIG. 1) that includes 3 components: a first end to receive a hind foot, an angled or bent portion to handle the hook of the leg, and a second end adapted to fit the upper thigh. The first end 120 has outer and inner sides 122 and 150 (FIG. 4) and further having a first cross-section 152 (FIG. 6) having a flexible opening to insert a dog's paw 123 (FIG. 6) therethrough. An elastic band can be used at the bottom of the first end to prevent slippage off a foot or up a leg.

The first end extends into an angled portion having a second cross-section 154 (FIG. 6) greater than the first cross-section 152. The system includes a second end with outer and inner sides 130 and 160 that is connected to the angled portion. The second end has a third cross-section 156 (FIG. 6) greater than the second cross-section 154. Additionally, the system includes a body portion 140 connected to the leg portion, the body portion 140 forming a double looping arrangement that fits securely on a body of the pet. The body portion 140 is further secured to the pet's belly using straps 190-192. The straps can include buckles or hook and loop with adjustability.

Figure 3:
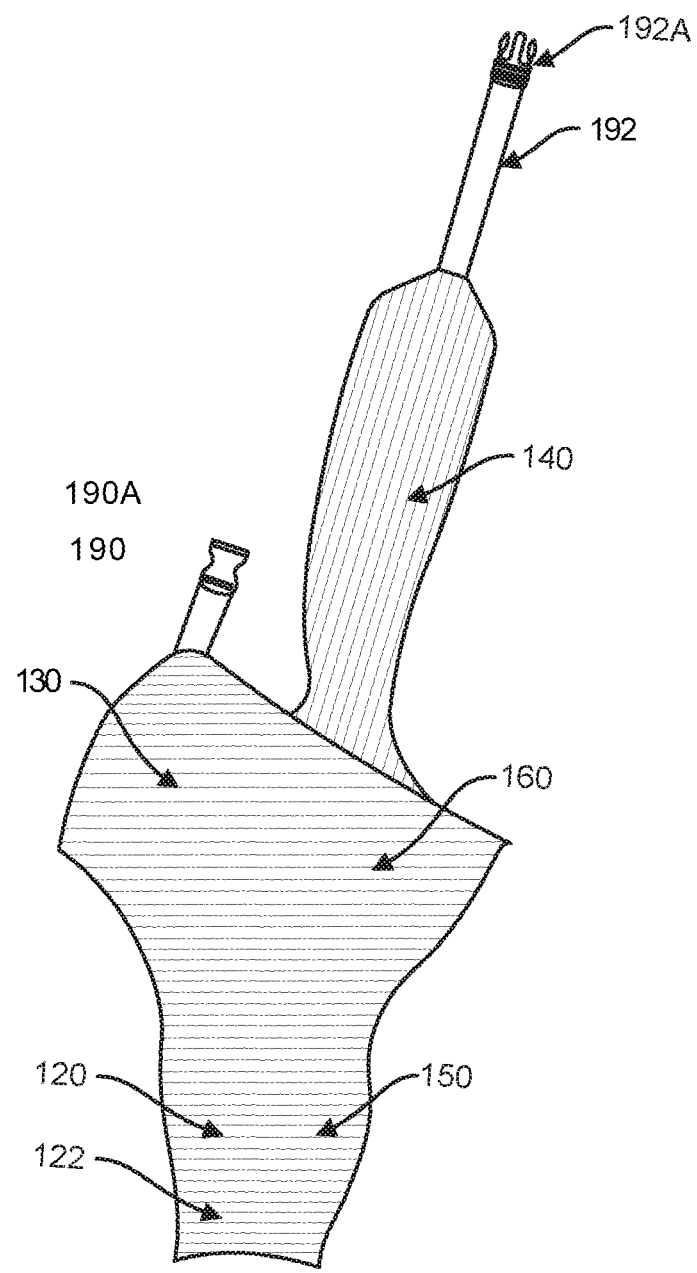
FIGS. 3-4 show a view of the inside and the outside of the sleeve system when the main sleeve seam has been removed and the sleeve system rests flat on a surface.
Figure 4:
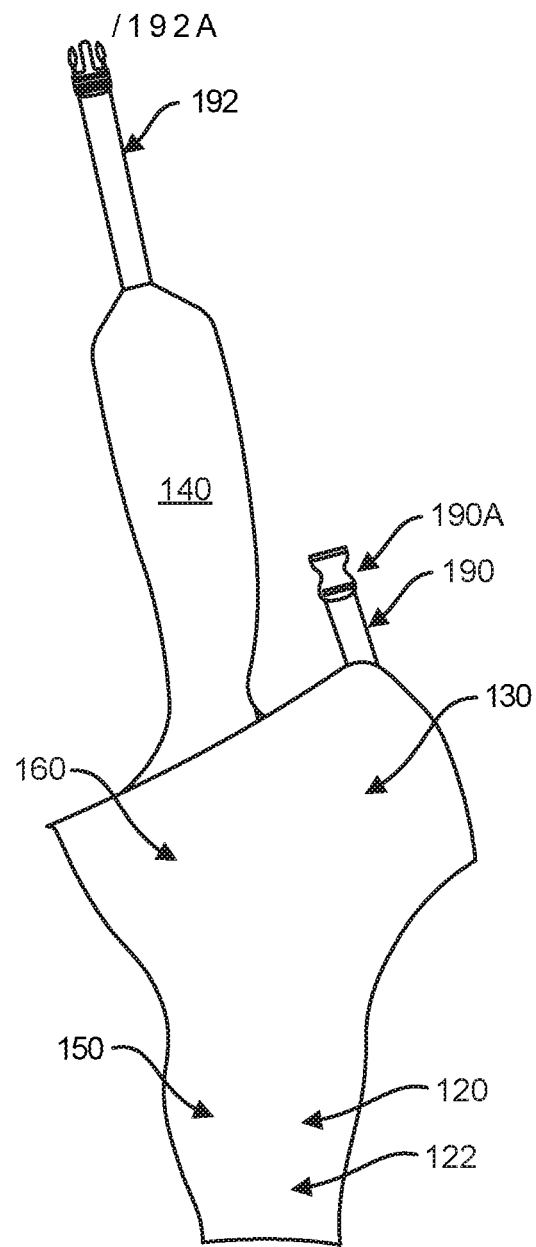

FIGS. 3-4 show a view of the inside and the outside of the sleeve system when the main sleeve seam has been removed and the sleeve system rests flat on a surface. FIG. 3 shows the sleeve system as cut flat to rest on a planar surface. The portions are glued together, sewn together or fused together by heat sealing to form a seam.

As shown in FIG. 4, two straps 192 and 190 connects a distal end of the body portion 140 to the distal portion of the second end at outer side 130. In the embodiment of FIG. 4, the straps 192 and 190 have a male end (192A) connected to the body portion and a female end (190A) connected to the second end. Preferably, the body portion 140 starts by first being wrapped under a pet's belly when used on a hind limb to avoid slippage off a pet's back. In one embodiment, the two straps include a male and female buckle fastener to provide reversibility.

Figure 5:
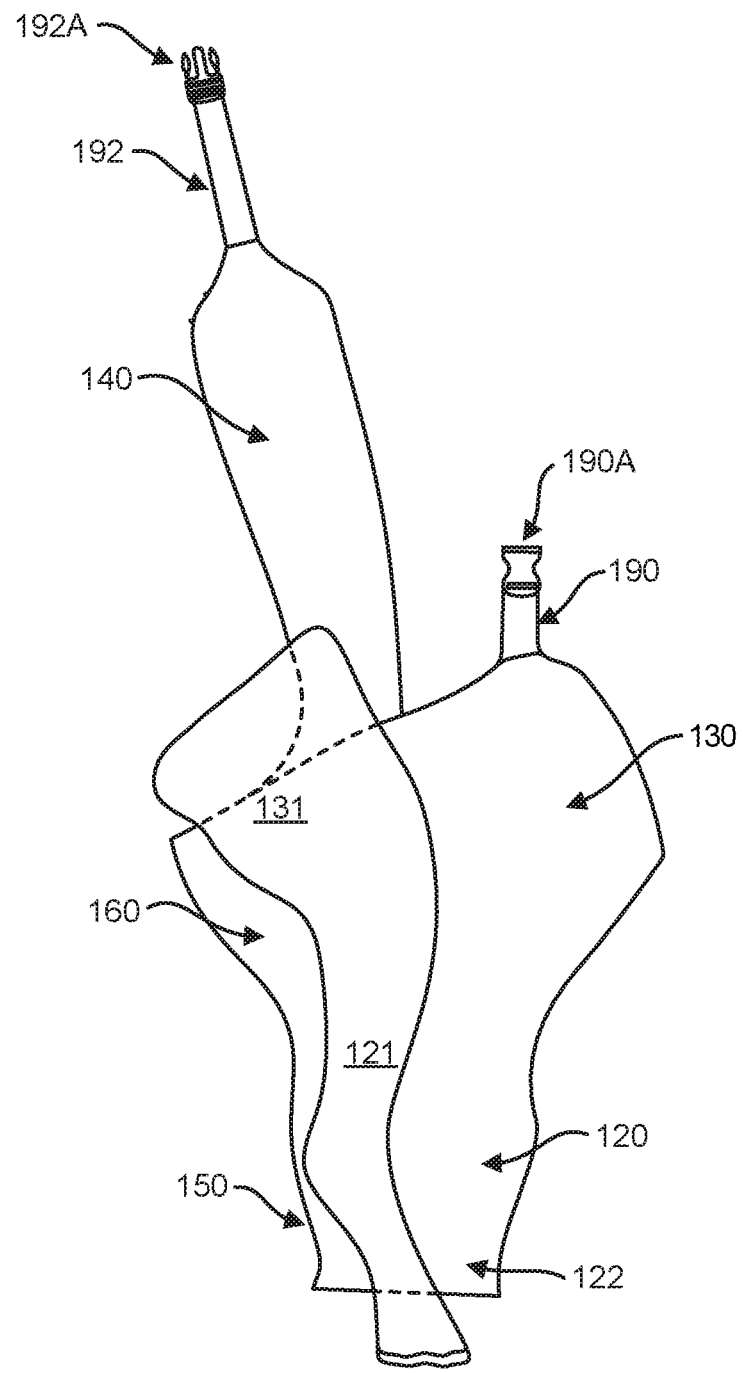
FIG. 5 shows a view of FIG. 4 with a leg to be protected on the surface of the sleeve system.
Figure 6:
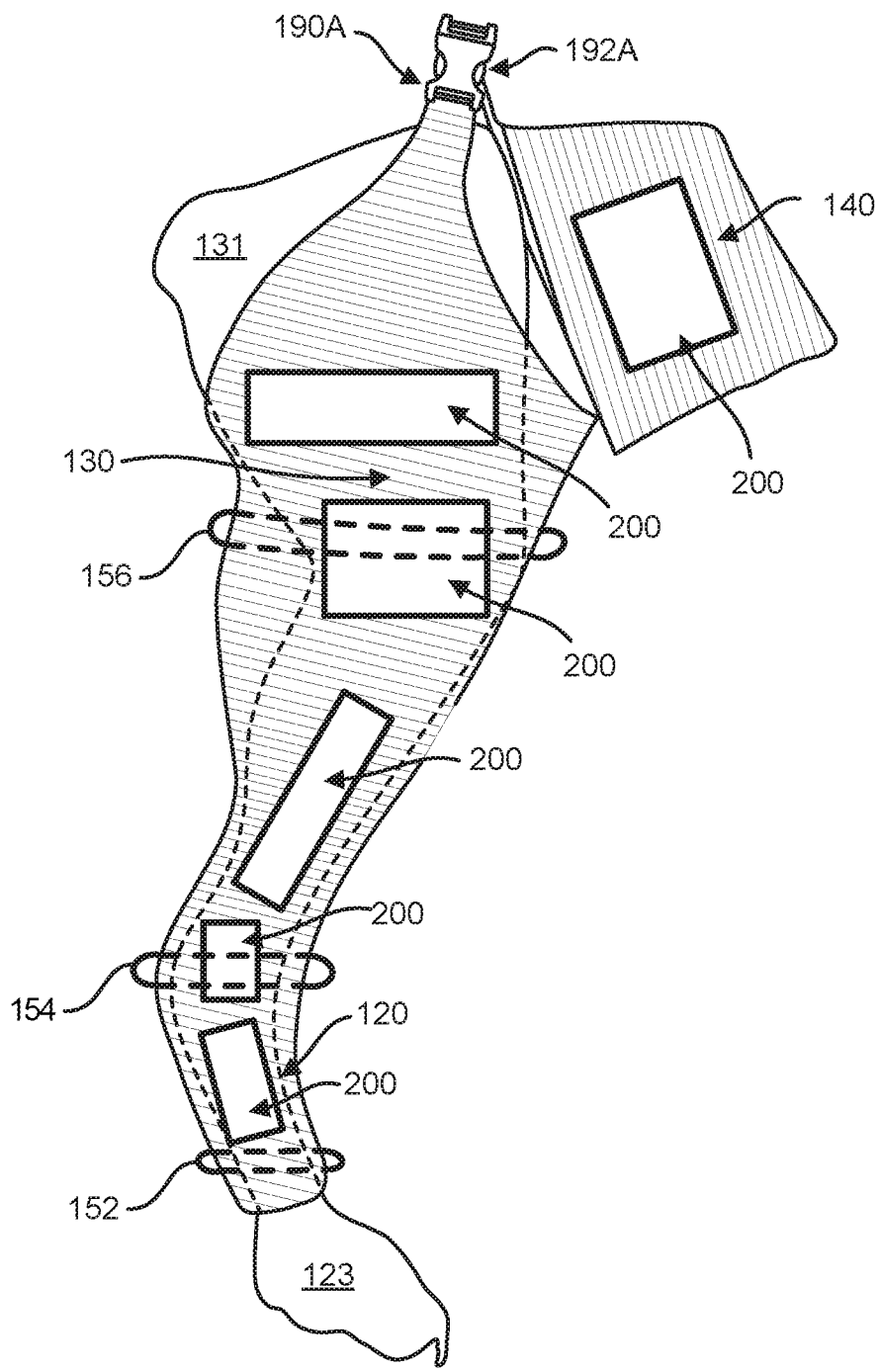
FIG. 6 shows an outside view of the leg inside the sleeve similar to FIG. 1

FIG. 5 shows a view of FIG. 4 with a dog's leg 121 (FIG. 5) to be protected on the surface of the sleeve system, while FIG. 6 shows the leg inside the sleeve with the remaining portion of the dog's upper leg 131 (FIG. 6) left minimally exposed. As shown in FIG. 6, the second end's outer side 130 is longer than the inner side 160. Further, the second end has a tapered shape in the direction of the pet's head. The second end eventually tapers to connect to the body portion which is a narrower than the second end and has an elongated shape.

Figure 7:
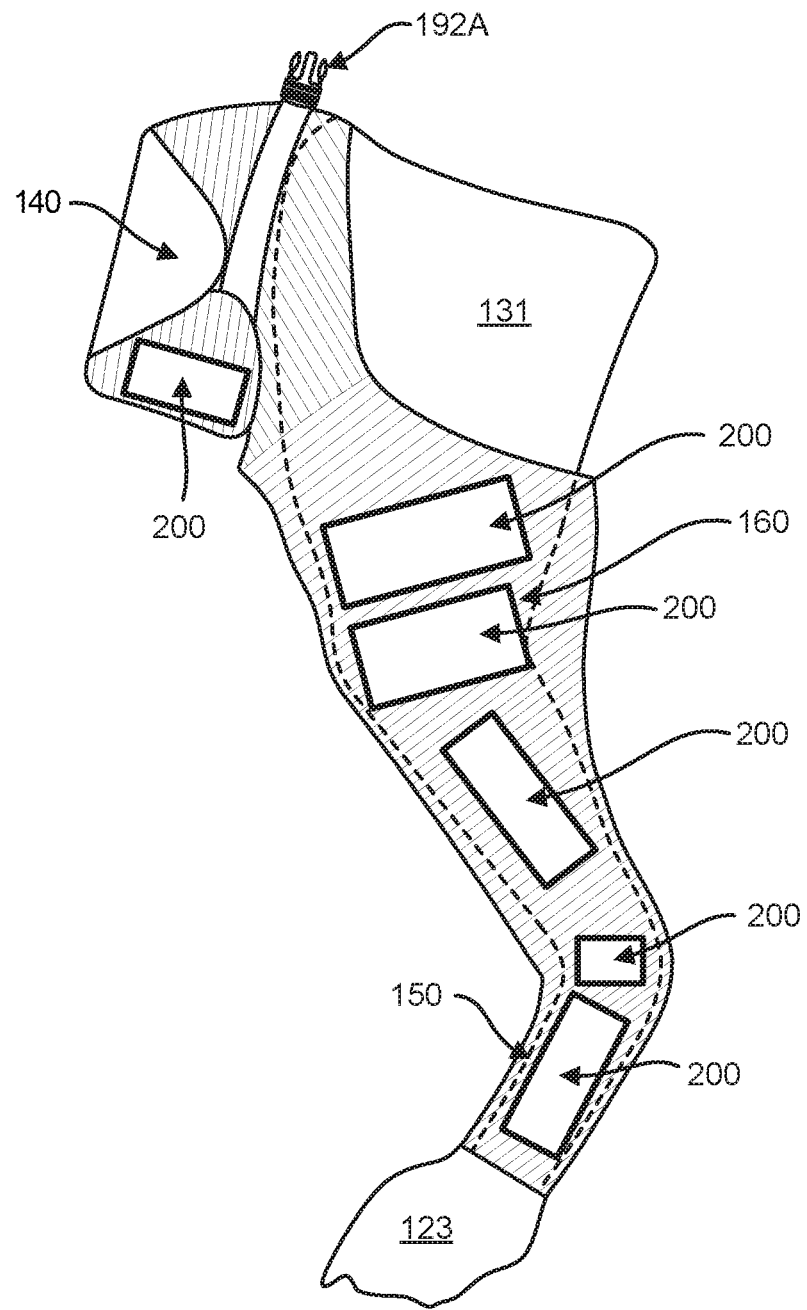
FIG. 7 shows an inside view of the leg inside the sleeve similar to FIG. 2

FIG. 7 shows an inside view of the leg inside the sleeve. As shown in FIG. 7, the inner side of the second end can have a curved shape at the top of the second portion. Alternatively, the inner side of the second portion can have a substantially L shaped cut at the top of the second end.

The body portion can have a U-shaped area cut-out or a penis hole in the body portion. One or more attachments 200 (FIG. 6 and FIG. 7) can be connected to the first end, angled portion, second end, or the body portion at a selected location on a body of the pet. One or more pet offensive materials can be secured to the attachment to the pet to repel it from licking the selected location. The offensive material includes pepper, metronidazole, bitter apple, or electric shock, among others. Wearable electronics can be used as an attachment to monitor or affect a pet. The wearable electronics monitor one of an activity level, a heart rate, a blood pressure, electrocardiogram (ECG) signal, or temperature, electrical muscle stimulators, among others. Additionally, a hook and loop combination can be positioned on a selected area for securing the proper fit to avoid slipping or bunching.

One method to protect a pet using a sleeve includes with the pet lying down to prevent injury or falling, placing the first end of the leg portion on a leg; stretching the first end of the sleeve over the pet's paw; moving the pet into a standing position; placing the body portion on an inside of the leg and wrapping the body portion around a belly of the pet towards an opposite leg; and strapping the body portion with the second end of the leg portion to produce a tight fit.

The Protective Sleeve for animals addresses the concerns of the animal disrupting the healing of the incisions and wounds. This is done with the use of a stretch fabric that is light weight, conforming, durable, and is moisture resistant. The blends of fabric used include polyester, lycra spandex, nylon, kevlar, cordura, or other such suitable fabrics. The sleeve features an elastic band at the bottom to prevent slippage off the foot or up the leg. The contours of the sleeve fit both the front and back legs. The body portion of the sleeve is designed to go under the belly of the pet when used on the hind limb, which enables the sleeve to stay in place without slipping off the back of the pet.

Straps with plastic buckle fasteners have been specifically chosen as they are the best means of fixation which preserve the reversibility of the sleeve. The ability of the sleeve to be turned inside out/be reversible is a key design feature and is what allows the same sleeve to fit all 4 limbs. The straps are adjustable to better fit a size range of animals. The straps are contoured in such a way to accommodate the male penis for urination and comfort. A u-shaped area has been cut out and in some sleeves a hole for the penis to exit has been incorporated. The short strap is sewn off center and towards the head of the pet to assist the longer strap in preventing the sleeve from slipping of the back of the animal. The two straps connect via a male and female buckle system. The sleeve is designed to be manufactured in multiple sizes and double sleeve configuration to accommodate additional surface area coverage and further insure the functionality. Attachments to the sleeve using hook and loop, magnetic or mechanical devices are being developed for multiple functions. The functions include but are not limited to holding offensive materials (peppers, metronidazole, or bitter apple) to the pet to repel it from licking the area. Hook and loop (velcro) can be used in some areas of the sleeve to optimize securing the proper fit to avoid slipping or bunching. Wearables to monitor or affect the animals activity level, heart rate, blood pressure, ECG, and temperature (prevent being left in car) are capable of being fit into the design. The figures show the pattern and dimensions for cutting the materials to be used in the construction of the sleeve.

The protective sleeve is best placed by first having the dog lie down on its side opposite of the leg upon which the sleeve is to be placed (lay down with the desired leg up). In other words, if the right leg is to be covered then the dog should lay on its left side. With the dog lying down to prevent injury or falling, the leg portion of the sleeve can be placed on the leg much like placing a pant leg or sock on a person. Once a substantial portion of the tubed portion is on the leg, the narrow diameter first end of the leg portion of the sleeve is stretched over the dogs paw. This first end of the leg portion of the sleeve is specifically designed not to later slip off or over the dog's paw as dogs tend to be bothered when any fabric is covering or underneath their footpads.

Once the leg portion of the sleeve is in place then the dog is allowed to stand to begin the placement of the body portion. It should be noted that the body portion is the longer of the two bands to which the strap and buckles are attached. The body portion of the sleeve should be on the medial or inside aspect of the leg. If the body portion is not starting from the inside aspect of the leg then the sleeve must be removed from the dogs leg (preferably with the dog laying down to prevent injury or falling), turned inside out and replaced on the leg.

With the body portion of the sleeve on the inside of the leg (dog standing) begin wrapping it around the belly towards the opposite leg. The body portion will pass in front of the opposite leg over the back of the dog, around the underneath side of the belly again, in front of the opposite leg again, and end on top of the dogs back. At this point the second end connected to the leg portion of the sleeve along with its strap and buckle should meet up with the body portion's strap and buckle over the top of the dogs back. Clasp the two portions of the buckle together and tighten the adjustable strap as needed to produce a tight fit.

Adjustments to the body portion of the sleeve can be made at this time to improve comfort and prevent bunching up of the fabric around the belly or the male dog's prepuce. It should also be noted at this time that manual shifting of the sleeve towards the dogs head should be promoted as the number one problem with improper fitting is for the sleeve to slip off of the dogs back towards the tail.

Additional adjustments and tightening may be required over time as the fabric conforms and stretches to the particular dogs fit.

Various modifications and alterations of the invention will become apparent to those skilled in the art without departing from the spirit and scope of the invention, which is defined by the accompanying claims.

It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

What is claimed is:

1. A reversible pet protection system for protecting a leg of a pet, the pet protection system comprising:
   a leg portion forming a conformable, permanently closed sleeve of stretch fabric and adapted to receive a first rear leg of a pet, the leg portion comprising:
      a first end having a first flexible aperture forming a distal end of the sleeve, the first end having a first cross-section;
      an angled portion continuing proximally from the first end and having a second cross-section larger than, and oriented caudally in relation to, the first cross-section; and
      a second end continuing proximally from the angled portion, tapering cranially, having a second flexible aperture at a proximal end of the sleeve, having a third cross-section larger than the second cross-section and oriented cranially in relation thereto, and having a lateral outer side longer than a medial inner side;
   an elongated body portion continuing from a proximal edge of the medial inner side;
   a first strap attached to a distal end of the body portion, and a first buckle fastener attached at a distal end of the first strap;
   a second strap attached to a proximal edge of the lateral outer side and oriented cranially, and a second buckle fastener attached at a distal end of the second strap;
   wherein:
      the body portion and strap are adapted to wrap around a body of the pet cranially to the first rear leg and a second rear leg of the pet such that the body portion first contacts a ventral portion of the body of the pet and subsequently passes over a dorsal portion thereof at least one time and at least one of the body portion and strap pass over the dorsal portion a second time, such that the strap is disposed upon and oriented substantially parallel with the body portion,
      after wrapping, the distal end of the strap is oriented in a ventral direction such that: the first buckle fastener registers with the second buckle fastener to secure the protection system on the first rear leg of the pet,
      after wrapping, the strap is substantially entirely disposed over at least one of the body portion and the leg portion such that the strap is not in direct contact with the pet, and
      the body portion, first strap, second strap, first buckle fastener, second buckle fastener, and leg portion are connected and arranged such that (a) when the sleeve is reversed by inverting the first end through the second aperture, the protection system fits a second rear leg of the pet as it previously fit the first rear leg, (b) when the cranial and caudal directions are reversed, the protection system fits a first front leg of the pet, and (c) when the sleeve is reversed by inverting the first end through the second aperture, and the cranial and caudal directions are reversed, the protection system fits a second front leg of the pet.

2. The pet protection system of claim 1, further comprising a U-shaped area cut out of a cranial edge of the elongated body portion and configured to align along a medial plane of a ventrum of the body of the pet.

3. The pet protection system of claim 1, the sleeve further comprising a main sleeve seam extending from the distal end to the proximal end of the sleeve, and
   wherein the pet protection system is configured such that when the sleeve is cut from the distal end to the proximal end, the entire protection system is configured to lay flat on a planar surface.

4. A reversible pet protection system for protecting a leg of a pet, the pet protection system comprising:
   a leg portion forming a permanently closed sleeve adapted to receive a first rear leg of a pet, the leg portion comprising:
      a first end having a first aperture forming a distal end of the sleeve, the first end having a first cross-section;
      an angled portion continuing proximally from the first end and having a second cross-section larger than, and oriented caudally in relation to, the first cross-section; and
      a second end continuing proximally from the angled portion, tapering cranially, having a second aperture at a proximal end of the sleeve, having a third cross-section larger than the second cross-section and oriented cranially in relation thereto, and having a lateral outer side and a medial inner side;
an elongated body portion continuing from a proximal edge of the medial inner side and configured to wrap entirely around the body of the pet at least once;
a strap attached to a distal end of the body portion;
a first fastener provided at a distal end of the strap;
and a second fastener connected to a proximal edge of the lateral outer side;
wherein:
the body portion and strap are adapted to wrap around a body of the pet cranially to the first rear leg and a second rear leg of the pet such that the body portion first contacts a ventral portion of the body of the pet and subsequently passes over a dorsal portion thereof, such that the strap is disposed upon the body portion after wrapping,
after wrapping, the distal end of the strap is oriented in a ventral direction such that the first fastener registers with the second fastener to secure the protection system on the first rear leg of the pet, and
the body portion, second fastener, and leg portion are connected and arranged such that when the sleeve is reversed by inverting the first end through the second aperture, the protection system fits a second rear leg of the pet as it previously fit the first rear leg.

5. The pet protection system of claim 4, wherein:
the first fastener and second fastener are a male buckle and a female buckle adapted to buckle together.

6. The pet protection system of claim 4, wherein:
the elongated body portion is adapted to completely encircle the body of the pet at least once, and
the strap is adapted to complete a second wrap around the body before the first fastener registers with the second fastener.

7. The pet protection system of claim 4, wherein:
the first aperture and second aperture are flexible, and
the first aperture is provided with an elastic band configured to resist proximal or distal movement of the first aperture in relation to a leg of the pet.

8. The pet protection system of claim 4, further comprising a U-shaped area cut out of a cranial edge of the elongated body portion and configured to align along a medial plane of a ventral portion of the body of the pet.

9. The pet protection system of claim 4, the sleeve further comprising a main sleeve seam extending from the distal end to the proximal end of the sleeve.

10. The pet protection system of claim 9, wherein the main sleeve seam comprises at least one of: a sewn seam, a heat sealed seam, and a glued seam.

11. The pet protection system of claim 4, wherein the leg portion is configured such that when the sleeve is cut from the distal end to the proximal end, the entire protection system is configured to lay flat on a planar surface.

12. The pet protection system of claim 4, wherein at least the body portion and the sleeve comprise a moisture-resistant stretch fabric.

13. The pet protection system of claim 4, wherein, when the first fastener registers with the second fastener, the second fastener is disposed dorsally and cranially to the third cross-section of the sleeve.

14. The pet protection system of claim 4, wherein:
the strap is a first strap,
the second fastener is connected to the proximal edge of the lateral outer side by a second strap, the second strap being oriented cranially, and
at least one of the first strap and second strap are adjustable in length, and,
when the first fastener registers with the second fastener, the second strap is oriented substantially parallel to a wing of an ilium of the pet, such that slipping towards a tail of the pet is prevented.

15. The pet protection system of claim 14, wherein the second strap is attached to the proximal edge of the lateral outer side in a cranial position relative to a center of the third cross-section.

16. The pet protection system of claim 4, further comprising at least one attachment provided on an outer surface of at least one of the leg portion and body portion.

17. The pet protection system of claim 16, further comprising at least one wearable electronics monitor removably fastened to the at least one attachment.

18. The pet protection system of claim 4 further comprising at least one pet offensive material.

19. The pet protection system of claim 4, wherein:
the pet protection system is configured to fit a first front leg of the pet as it fit the first rear leg by reversing cranial and caudal directions of the pet protection system, and
is further configured to fit a second front leg of the pet as it fit the first front leg by both reversing cranial and caudal directions and by inverting the first end through the second aperture.

20. The pet protection system of claim 4, wherein after wrapping, the strap is substantially entirely disposed over at least one of the body portion and the leg portion such that the strap is not in direct contact with the pet.

* * * * *